United States Patent [19]
Miraki

[11] Patent Number: 5,439,447
[45] Date of Patent: Aug. 8, 1995

[54] BALLOON DILATION CATHETER WITH HYPOTUBE

[75] Inventor: Manouchehr Miraki, Aliso Viejo, Calif.

[73] Assignee: Baxter International Inc., Deerfield, Ill.

[21] Appl. No.: 333,911

[22] Filed: Nov. 3, 1994

Related U.S. Application Data

[63] Continuation of Ser. No. 194,086, Feb. 9, 1994, Pat. No. 5,387,193.

[51] Int. Cl.⁶ ............................................. A61M 29/00
[52] U.S. Cl. ....................................... 604/96; 606/194
[58] Field of Search .................................. 604/96–104, 604/164, 166, 167, 160, 158; 606/191–195

[56] References Cited

U.S. PATENT DOCUMENTS 5,261,879 11/1993 Brill ........................................ 604/96
5,306,247 4/1994 Pfenninger ........................... 606/194

*Primary Examiner*—John D. Yasko
*Attorney, Agent, or Firm*—Raymond Sun

[57] ABSTRACT

A balloon dilation catheter includes a distal monorail section, to which a balloon is secured, and a catheter body tube including a monorail section. A guide tube extends through the balloon and has a proximal end sealed to a guide wire port in the body tube. A guide wire extends along the body tube and through the guide tube. To stiffen the body tube while maintaining maximized fluid flow area, a stainless steel hypotube extends through the proximal body tube, has a distal opening positioned adjacent the guide wire port and a solid reinforcing tapered distal end section that extends across the guide port. The hypotube can be fixed or removable. Alternatively, the hypotube divides the interior of the proximal body tube section into two separate flow passages to enable positive purging.

6 Claims, 4 Drawing Sheets

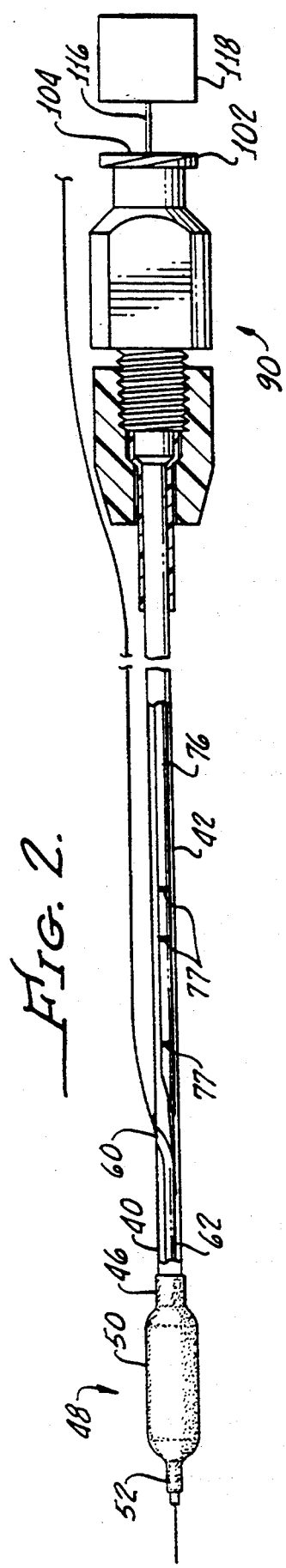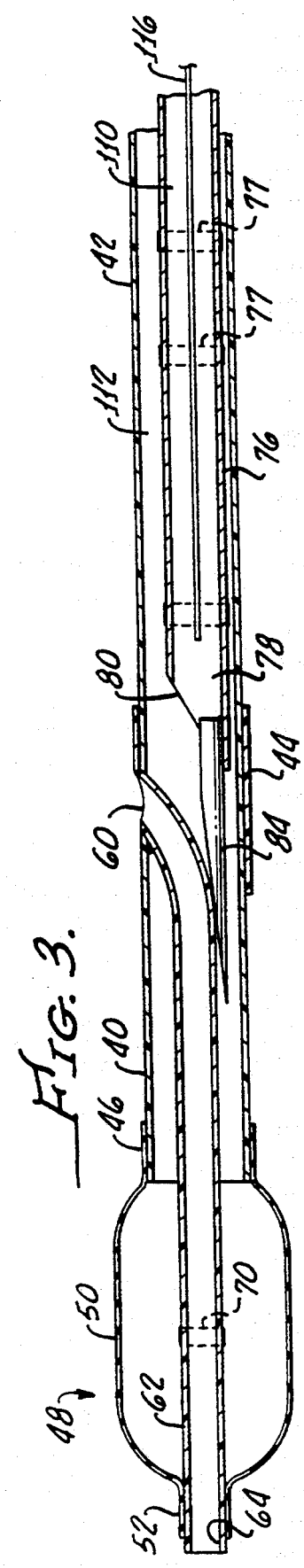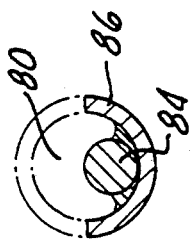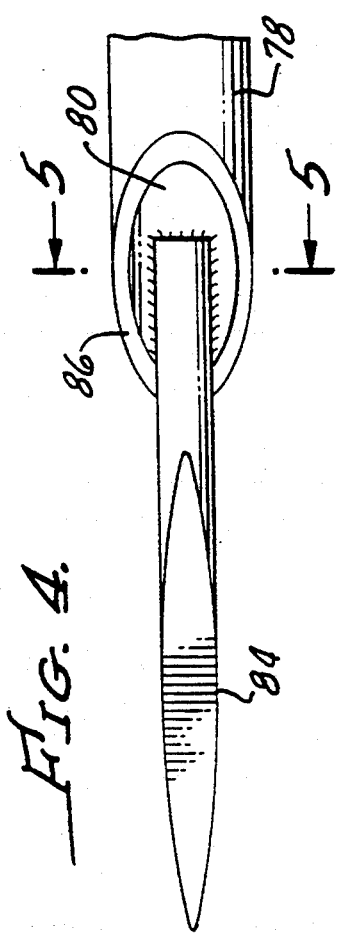

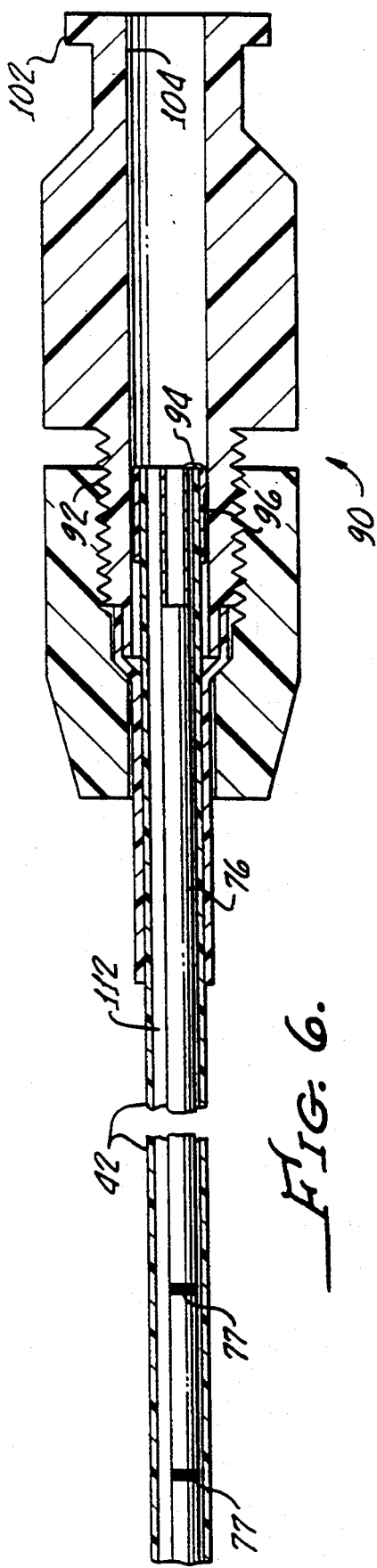
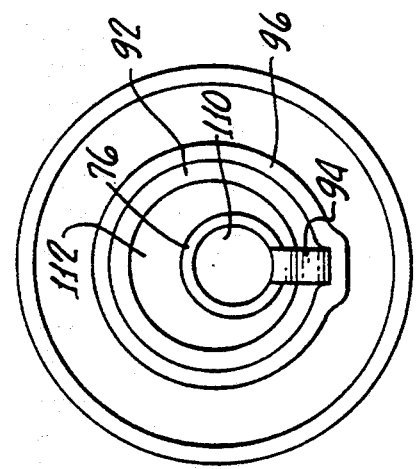
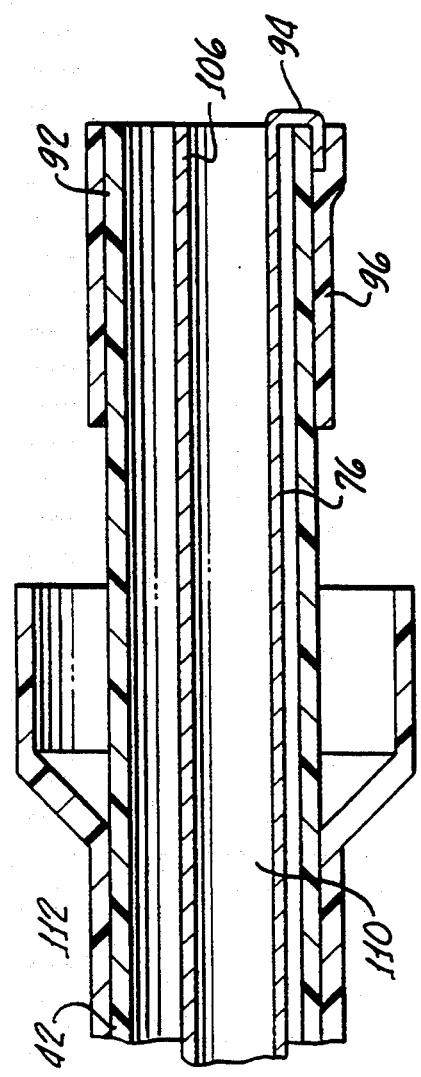

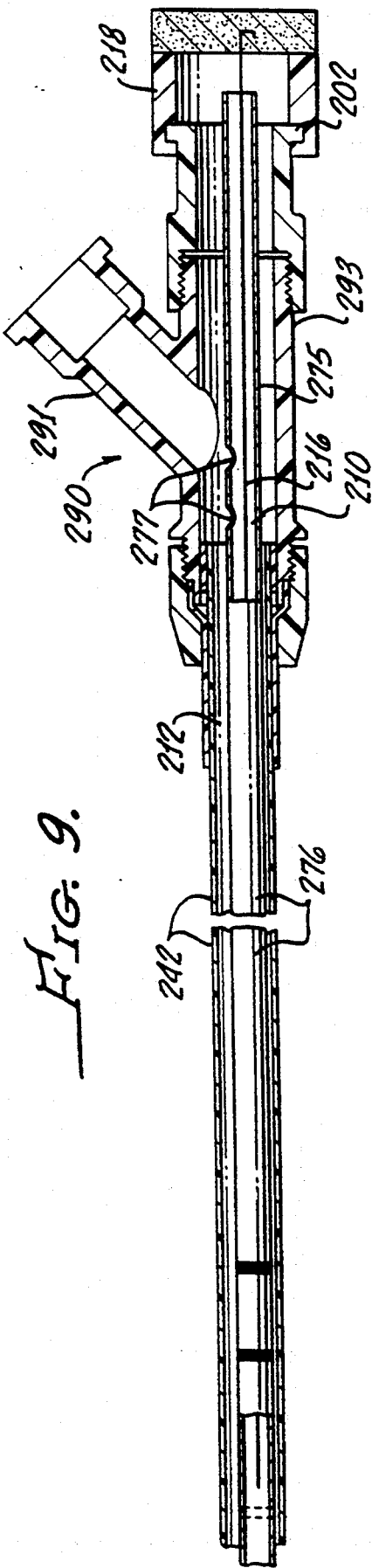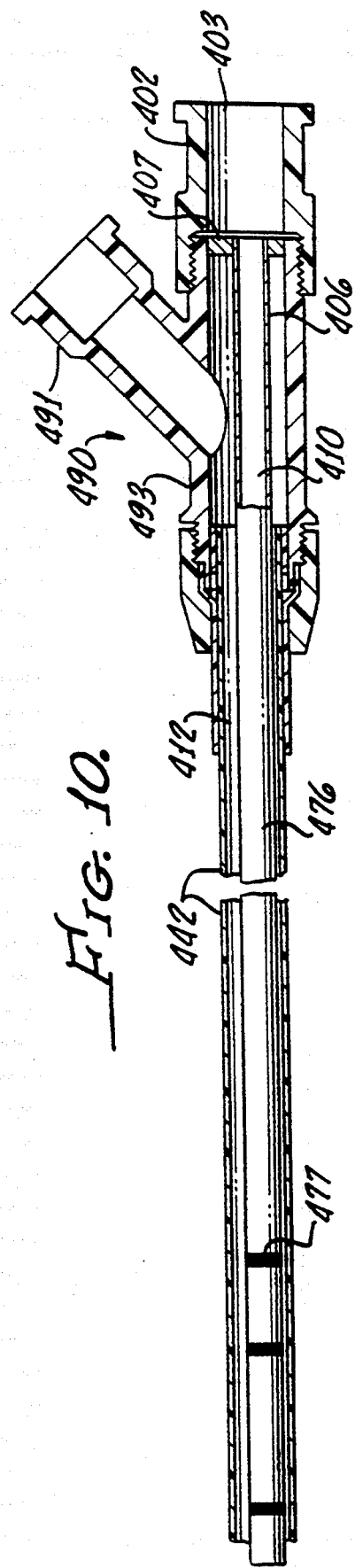

BALLOON DILATION CATHETER WITH HYPOTUBE

This application is a continuation of U.S. application Ser. No. 08/194,086 filed on Feb. 9, 1994 now U.S. Pat. No. 5,387,193.

BACKGROUND OF THE INVENTION

1. Field of the Invention

The present invention relates to balloon dilation catheters, and more particularly concerns a catheter having improved pushability, trackability and time of inflation.

2. Description of Relevant Art

Therapeutic balloon dilation catheters, used for balloon angioplasty, are known in the art which are of the so-called "monorail" configuration. Such monorail catheters generally have a comparatively short distal monorail portion of the catheter slidably received over a guide wire. This distal portion includes an expansible dilation balloon. Other than the comparatively short distal portion of the guide wire received within the catheter, the remainder of the guide wire is exposed externally of the catheter. The monorail portion is coupled with a catheter body tube formed of a flexible material that allows the catheter to be pushed through curved vascular pathways and also enables passage of a balloon inflation fluid. Some typical balloon dilation catheters are shown in U.S. Pat. Nos. 5,217,482 to Keith; 4,762,129 to Bonzel; 5,061,273 to Yock; and 4,748,982 to Horzewski et al.

During angioplasty a guide catheter with a guide wire therein is initially inserted into a patient and serves both to guide a therapeutic catheter along the vascular pathway to a location close to the heart and to protect the patient's blood vessels from trauma which could be caused by contact with the therapeutic catheter.

The guide catheter, with the guide wire in place, is pushed along the vascular pathway until the distal end of the guide catheter reaches a position adjacent but somewhat short of the position at which the angioplasty is to take place. Beyond the distal end of the guide catheter the guide wire is extended through the stenosis of the vascular area that is to be treated. A therapeutic catheter, having the expansible dilation balloon on a distal extremity, is inserted into the guide catheter and over the guide wire, which extends through the monorail section along the guide wire of the therapeutic catheter, so that the catheter is guided beyond the end of the guide catheter to the treatment location. While the balloon is positioned at the treatment location, a dilation fluid is injected into the therapeutic catheter body tube and inflates the thin wall expansible dilation balloon to enlarge the stenosis.

The therapeutic catheter is formed of a body tube that performs a number of functions. It provides the axial drive or push that moves the collapsed and folded balloon at the distal end through the vascular pathways. For this reason certain proximal portions must be relatively stiff and have a high "pushability", although the catheter bends in the vascular pathway. The catheter body tube also forms a lumen that provides a flow path for dilation fluid. In order to decrease inflation and dilation time, the lumen cross-section must be as large as possible and still fit within the guide catheter, which in turn must fit within the vascular pathway.

In certain types of angioplasty it is desirable to provide a positive purge of fluid within the dilation balloon to ensure that the latter is free of air before using the therapeutic catheter. To facilitate positive purging, the body tubes of some balloon dilation catheters are formed of a single plastic extrusion having a triad of three side-by-side integral lumens, one to flow fluid distally, a second to flow fluid proximally, and a third to accept an axially insertable stiffening wire to stiffen and strengthen the integral extruded plastic side-by-side tubes. Such an arrangement is expensive and of relatively large diameter, limiting its use to larger vascular pathways. Its pushability is relatively low, requiring a stiffening wire which uses a significant part of the cross-section of the total flow area available. U.S. Pat. No. 5,061,273 to Yock shows a catheter having a multilumen body tube.

If the conventional therapeutic catheter body tube is made of a flexible plastic, it loses pushability and may not be able to drive the balloon to its proper position. If made of a stiffer plastic, it may not readily follow the curvature of vascular pathways. If it is stiffened with an integral wire, flow area is lost and inflation and deflation time is increased. Therefore, prior catheters have involved a compromise among several conflicting requirements.

In the monorail type of catheter, both the guide tube that extends through the inflation balloon and the guide wire itself exit the therapeutic catheter body at a guide wire port in the side wall of the body tube. This area of the catheter is weakened by the guide wire port and has a tendency to kink severely as the catheter is moved along the vascular pathway, and as the wire traverses the guide wire port.

Accordingly, it is an object of the present invention to provide a balloon dilation catheter that avoids or minimizes above mentioned problems.

SUMMARY OF THE INVENTION

In carrying out principles of the present invention, according to a preferred embodiment thereof, elongated proximal and distal body tube sections are fused to one another with an expansible dilation balloon having a proximal end bonded to the distal end of the distal body tube. The two body tube sections collectively form a therapeutic catheter body tube and have a guide wire port therein proximally of the proximal end of the expansible dilation balloon. A guide tube extends through the balloon and through the port of the body fuse area, having a distal end opening at and bonded to the distal end of the balloon and having a proximal end opening at and sealed to the guide wire port. Within the body tube is a relatively stiff hypotube, having an open proximal end adjacent the proximal end of the proximal body tube section and an open distal end adjacent the guide wire port. The hypotube, together with the catheter body tube, form inner and outer nested flow passages for flow of fluid therethrough. The hypotube is provided with a stiffening distal solid taper wire section extending within the catheter body tube from a proximal portion to a distal portion of the guide wire port. The hypotube may be fixedly secured relative to the body tube, or it may be removable. In one embodiment, the inner and outer flow passages are sealed separately from one another so as to provide for a positive purging operation, flowing fluid distally toward the balloon through one of the passages and flowing fluid proximally from the balloon through the other of the passages. The hypotube provides stiffening for the proximal body tube section without any significant decrease in flow passage area. This provides improved pushability, improved trackability, and decreased time of inflation and deflation.

BRIEF DESCRIPTION OF THE DRAWINGS

FIG. 2 is a longitudinal section of a therapeutic catheter embodying principles of the present invention.

FIG. 3 is an enlarged section of the distal end of the catheter of FIG. 2.

FIG. 4 is an enlarged fragmentary view of a distal end of the hypotube used in the catheter of FIGS. 2 and 3.

FIG. 5 is a section taken on lines 5—5 of FIG. 4.

FIG. 6 is a longitudinal section of the proximal end of the therapeutic catheter of FIGS. 2 and 3.

FIGS. 7 and 8 show details of the attachment of the proximal end of the hypotube.

FIG. 9 is an enlarged sectional view of a portion of the proximal end of a modified therapeutic catheter.

FIG. 10 is a view like that of FIG. 9 showing still another embodiment.

DETAILED DESCRIPTION OF EXEMPLARY EMBODIMENTS

Figure 1:
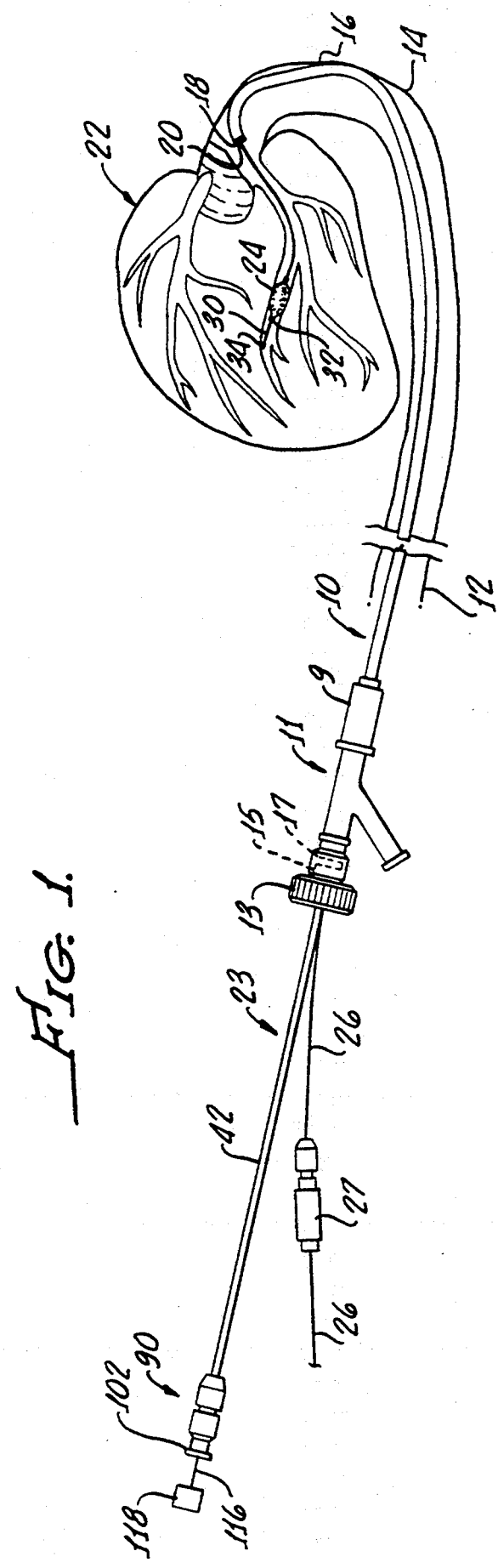
FIG. 1 schematically represents a guide catheter which is introduced into a patient's femoral artery and which extends at its distal end around the aortic arch to terminate at a location adjacent the patient's heart. A therapeutic catheter extends through the guide catheter to the patient's heart.

As illustrated in FIG. 1, a tubular guide catheter 10 is introduced into a patient's femoral artery 12 and caused to extend upwardly to terminate at the aortic arch 14. The guide catheter 10 includes a distal re-curve section 16 which allows a distal end opening 20 of the guide catheter to be disposed toward the patient's heart 22. At the proximal end of the guide catheter 10 is mounted a rotatable hemostatic adapter 9 and a Y or two-arm connector or adapter 11 which is mounted on the rotatable adapter. The Y connector 11 is provided with a knurled knob 13 which carries a threaded valve member 15 that carries an O-ring 17, which is adapted to be urged into sealing engagement with the exterior of a therapeutic balloon dilation catheter 23 that is inserted into the guide catheter 10. Therapeutic balloon dilation catheter 23 has an expansible dilation balloon 24 on its distal end. Catheter 23 is introduced into the guide catheter 10 along a guide wire 26 that has a proximal end secured to a manually manipulated and removable torque member 27. Initially the guide wire 26 and the guide catheter 10 are inserted into the femoral artery, with the distal end of the guide catheter stopping short of the location of the stenosis to be treated. The guide wire, which extends through the guide catheter, then is pushed distally beyond the end of the guide catheter and is manipulated by rotation of torque 27 to enter the selected artery and to pass through the stenosis or area to be treated. The guide wire has a very flexible distal end portion 30 that extends into the area to be treated. This distal end portion 30 projects distally from the open end of the guide catheter and carries a radiopaque marker 34 on its tip, by which a physician can visualize the guide wire location and steer the guide wire to the treatment site.

With the guide catheter and guide wire in place, the therapeutic catheter 23 is then slid over the proximal end of the guide wire (with torquer 27 removed) which projects axially from the proximal end of the guide catheter 10. The therapeutic catheter 23 is axially pushed into and along the length of the interior of the guide catheter 10 until its dilation balloon 24 extends distally beyond the end 18 of the guide catheter and into the desired treatment location to which it is guided by guide wire 26. The dilation balloon also includes a radiopaque marker or band, as will be described more particularly below.

FIG. 2 shows the therapeutic catheter and guide wire, both of which are inserted into and through the lumen of the guide catheter interior. The guide catheter is not shown in FIGS. 2-8. FIG. 2 shows the entire therapeutic catheter. FIG. 3 shows the distal end of the therapeutic catheter. The catheter is formed of a distal body tube section 40 made of, for example, a 70/30 polyethylene tubing (employing 70% high density polyethylene and 30% low density polyethylene) to provide a relatively more flexible distal body tube section. To the proximal end of the distal body tube section 40 is fused a proximal body tube section 42, with the two being fused together at a fuse area 44 (FIG. 3). The proximal body tube section 42 is stiffer, being made of a 90/10 polyethylene tubing (90% high density polyethylene and 10% low density polyethylene).

To the distal end of the distal body tube 40 is bonded, as at 46, an expansible dilation balloon 48, having a expansible wall 50 and a distal end 52. A slit 60 is formed in the fused area 44 between the distal and proximal body tubes. A flexible guide tube 62 extends axially within the dilation balloon and has a distal end 64 bonded to and sealing the distal end 52 of the inflation balloon. The guide tube 62 extends proximally through the proximal end of the dilation balloon and through the distal body tube 40 to the slit 60. This slit defines a guide wire port in the wall of the fused area between the distal and proximal tube sections. The proximal open end of the guide tube is sealed to the guide wire port 60.

When the therapeutic catheter is used, guide wire 26 (shown in FIGS. 1 and 2, but not in other figures) extends along the exterior of the proximal body tube 42, through the guide wire port 60, through the guide tube 62, and through the distal open end 64 of the guide tube to provide a guide wire distal section 30 (FIG. 1) that extends outwardly beyond the distal end of the dilation balloon. A radiopaque band 70 encircles an intermediate area of the guide tube 62, within the balloon, and is secured thereto by any suitable means, such as a sleeve (not shown) that extends over a portion of the guide tube 60 and over the radiopaque band 70.

Mounted within the proximal body tube 42 and extending from a point near the proximal end thereof distally toward the fused area 44 is a hypotube 76 formed of thin wall, hollow, stainless steel, relatively stiff tubing. The hypotube has a distal end 78 (FIG. 3) that is formed with a distal opening 80 and has a distal stiffening section 84 fixed thereto. The distal end of the hypotube is cut off at a slant, leaving a portion of the end of the hypotube of a height of about 0.016 inches at the distal tip and a distal opening 80 in its distal end. A solid tapered stainless steel wire 84, having a small distal end of about 0.003 inches and a larger proximal end of about 0.016 inches, has its proximal end positioned in and welded to the distal end 78 of the hypotube (see FIGS. 4 and 5) to provide a tapered solid catheter stiffening extension for the hypotube. Thus the distal end portion of the hypotube includes both an opening 80 communicating with the interior of the hypotube (and the interior of the distal body tube section 40) and a solid stiffening tapered wire section 84. The tapered wire section 84 extends from the distal end of the hypotube distally across the entire length of the fused area 44 to a point distally of the fused area. As shown in FIG. 5, the tapered solid wire 84 is seated in the upwardly open distal end 78 of the hypotube and is welded thereto. The tapered stiffening wire 84 extends completely across and under the guide wire port 60, beyond both sides thereof, and provides an increased rigidity to the portion of the catheter in which the guide wire port is formed. This minimizes a tendency of the weakened (by port 60) area of the catheter to kink as the therapeutic catheter is moved in and out of the guide catheter along the guide wire, as will be described more particularly below.

As illustrated in FIG. 6, the proximal body tube 42 section extends proximally to a proximal connection fixture 90, wherein the proximal end 92 of the proximal body tube section 42 is securely bonded. The proximal connection fixture, in some embodiments, includes an angulated fitting (as shown in FIGS. 9 and 10). However, the fixture of the embodiment of FIGS. 2 through 8 has a straight through configuration, as best seen in FIGS. 2 and 6. The fixture 90 of FIGS. 2 and 6 extends axially for connection to a luer fitting 102, having a proximal port 104 that opens axially to the proximal end of the fixture.

Hypotube 76 includes a proximal end 106 that is fixedly connected to the proximal body tube section 76 by a hook 94 which extends radially outwardly from the hypotube proximal end and is bent back around the end 92 of the proximal body tube section 76, as best seen in FIGS. 7 and 8. Hook 94 is formed as an integral part of the proximal end of the hypotube and bent to its hook shape. A short length of heat shrink tube 96 is bonded to and around the proximal end of the body tube section 76 and the bent end of the hook is clamped between the heat shrink tube and the body tube section.

The hypotube 76 and the proximal body tube section 42 divide the interior of the therapeutic catheter body tube into inner and outer nested fluid flow passages 110,112 (FIG. 7). The inner passage is formed by the interior of the hypotube, whereas the outer passage is an annular passage formed between the exterior of the hypotube and the interior of the proximal body tube section. These two passages, in the arrangement of FIGS. 2-8, are in fluid communication with one another at both proximal and distal ends of the hypotube, since the connecting hook 94 will allow fluid injected through the axial opening 104 to flow into proximal ends of both the inner and outer passages 110, 112. A stiffening stylet wire 116 (FIGS. 2 and 3, but not shown in FIGS. 6 and 7) has a proximal end fixedly secured to an end cap 118 and extends through the axial opening 104, through the fixture 90 and through the length of the hypotube 76 to its distal end. The cap 118 is detachably engaged with the luer fitting 102, and thus the stiffening stylet may be removably inserted into the fixture and into the interior of the hypotube. With the stylet wire removed, the axial opening 104 may be used for inflation and deflation. Application of inflation fluid to the fixture 90 will cause fluid to flow through both the inner and outer flow passages 110,112. Similarly, deflation may occur by flow of fluid through both the inner and outer passages upon application of a negative pressure to the axial opening 104.

In operation of the device, the guide catheter 10, with a guide wire positioned therein, is inserted into the femoral artery and pushed along the vascular pathway until it reaches the position illustrated in FIG. 1 with the distal end of the guide catheter positioned at the inner end of the aortic arch. The guide catheter remains in this position and the guide wire is then pushed further into the heart and maneuvered until it enters the desired artery. This maneuvering is assisted by the radiopaque tip 34, which helps the physician steer the flexible tip of the guide wire to the treatment site. Now the distal end of the therapeutic catheter, via its distal opening 64, is inserted over the proximal end of the guide wire (which is outside of the patient's body and has torque 27 removed) and pushed along the guide wire, within the guide catheter, causing the guide wire to traverse the inner guide tube 62 and the guide port as the distal end of the. therapeutic catheter and the expansible dilation balloon are pushed along the guide wire within the interior of the guide catheter. At this time the expansible dilation balloon, which is illustrated in FIGS. 1, 2 and 3 in inflated condition, is in collapsed folded condition so as to present an exterior size that is not significantly larger than the exterior size of the distal body tube 40. As the therapeutic catheter is pushed along the guide wire inside of the guide catheter, its distal end emerges from the distal opening end 18 of the guide catheter, and its position can be effectively observed by the physician with the help of the radiopaque band 70 on the guide tube 62. The collapsed dilation balloon continues to pass along the guide wire until it enters the treatment area where its motion is stopped. During this part of the procedure the presence of the hypotube greatly enhances the pushability of the therapeutic catheter. Pushability may be further enhanced by the insertion of stylet wire 116 into the interior of the hypotube to extend to the fused area 44. The fact that the stiffened proximal body tube section has a distal end which is relatively close to the proximal end of the dilation balloon further enhances trackability of the apparatus, since the axial compressive force exerted along the stiffened proximal body tube section is transferred to the more flexible distal body tube section, and thence to the dilation balloon, at a point that is not far from the proximal end of the balloon.

At this point in the procedure, the balloon will be inflated. If a stylet has been inserted, this will be removed. Inflation fluid is applied via opening 104 in fixture 90 to effectively fill the interior of the proximal connection fixture 90 and force fluid through both inner and outer flow passages 110,112. The presence of the thin wall hypotube blocks very little of the cross-sectional area of the total flow passage within the therapeutic catheter body tube, and inflation may occur at a relatively rapid rate. So too, deflation will occur at a relatively rapid rate as a negative pressure is applied to fixture 90.

If necessary, the entire therapeutic catheter may be readily and rapidly, withdrawn after deflation of the balloon, by pulling it proximally to cause the balloon and guide tube to ride along the guide wire. If a larger or different dilation balloon is required, a second therapeutic catheter with an appropriate dilation balloon then has its most distal end inserted over the free proximal end of the guide wire and the second therapeutic catheter is inserted just as is the first, with the prior procedure then repeated. The tapered wire distal end section 84 of the hypotube extends completely across the fused area of the body tubes and across the guide wire port to stiffen this weakened section and body tube and minimize the potential for kinking of the therapeutic catheter during insertion and withdrawal thereof.

FIG. 9 illustrates the proximal end of a modified form of therapeutic catheter. In this embodiment the distal end of the therapeutic catheter (not shown in FIG. 9) may be identical to the distal end of the catheter illustrated in FIGS. 2 through 8. In the arrangement of FIG. 9, however, the hypotube is made removable rather than being fixed to and within the proximal connection fixture. In FIG. 9 parts that correspond to similar parts of FIG. 2 through 8 are designated by the same reference numerals, having a prefix "2" added, so that, for example, proximal body tube section 242 of FIG. 9 corresponds to proximal body tube section 42 of FIG. 2. The proximal body tube section 242 has its proximal end secured to and within a Y type proximal connection fixture 290, having an angulated branch 291 and an axial branch 293. Angulated branch 291 communicates with the interior of the connection fixture. The latter has secured to the proximal end of its axial branch a luer fitting 202 that has a threadably engageable and detachable sealing cap 218. In this embodiment hypotube 276, which has a distal end identical to the distal end of the hypotube 76 of FIG. 2, extends at its proximal end entirely through the proximal connection fixture 290 and through the luer fitting 202 to a fixed connection to detachable cap 218. The proximal end portion 275 (within fixture 290) of hypotube 276, in this arrangement, is formed with a plurality of apertures 277 that provide for fluid communication between the interior of the proximal connection fixture 290 and the interior of the hypotube. Thus, these apertures 277 effectively provide fluid communication between the inner and outer flow passages 210, 212 at the proximal end of the catheter. A stylet 216 secured to cap 218 extends through the hypotube to provide further stiffening, if deemed necessary or desirable.

The arrangement of FIG. 9 is used substantially in the same manner as is the embodiment of FIGS. 2 through 8. With the hypotube in place and cap 218 secured to luer fitting 202, inflation and deflation can be accomplished rapidly in the same manner as it is accomplished with the embodiment of FIGS. 2 through 8. Inflation fluid is passed through the branch 291 into the outer annular passage within the fixture and flows through holes 277 to the inner passage 210. However, in the arrangement of FIG. 9 the hypotube may be entirely removed and the luer fitting 202 sealed by a second cap (not shown) so that an even greater rate of inflation and deflation can be accomplished, when the even very small amount of cross-sectional obstruction of the hypotube and stylet are removed. The arrangement of FIG. 9 has, in addition, all of the advantages of the arrangement of FIGS. 2 through 8, including enhanced pushability and trackability and faster inflation and deflation time. With the hypotube and stylet wire within the body tube, pushability is enhanced for insertion of the catheter, and rapid inflation and deflation can be accomplished. After insertion, the hypotube and stylet can be removed for even faster inflation and deflation.

Illustrated in FIG. 10 is a modification of the arrangement of FIGS. 2 through 8, configured to provide for positive purging. FIG. 10 again illustrates only the proximal portion of the therapeutic catheter, which has a distal portion identical to the distal portion of the catheter of FIGS. 2 through 8. Only the proximal end of the catheter is changed. In the arrangement of FIG. 10 corresponding parts are designated by corresponding reference numerals with the prefix "4" added thereto, so that, for example, proximal body tube section 42 of FIG. 5 corresponds to proximal body tube section 442 of FIG. 10. So, too, a hypotube 476 and radiopaque markers 477, corresponding to hypotube 76 and markers 77, are mounted in proximal body tube section 442. The hypotube, positioned within the proximal body tube section 442, has a distal end (not shown in FIG. 10) that is identical to the hypotube distal end illustrated in FIGS. 2 through 5, having the same relation to the other distal portions of the therapeutic catheter as is illustrated in FIGS. 2 through 5. In the arrangement of FIG. 10 a proximal Y connection fixture 490 is fixed to the proximal end of the proximal body tube section 442 and is provided with an angulated fitting branch 491 and an axial branch 493. Fixture 490 has a proximal end fixedly carrying an axial luer fitting 402, having an interior bore 403. The proximal end 406 of the hypotube 442 is fixed to and sealed to a mounting collar 407 fixed in the proximal end of the fixture 490. This seals inner passage 410 from outer passage 412. The hypotube has an open proximal end opening into the bore 403 of fitting 402 and thus is open to the atmosphere via the fitting 402. In this arrangement there are no holes in the proximal end of the hypotube and the inner passage 410 of the therapeutic catheter (as within the hypotube) is isolated and sealed from the outer annular passage 412 at the proximal portion of the instrument.

In this arrangement pushability and trackability are enhanced just as in the arrangements previously described. In fact, if deemed necessary or desirable, a stiffening stylet wire (not shown in FIG. 10) may be inserted into the hypotube to further enhance pushability. Inflation and deflation time may be increased by providing for inflation fluid to be applied simultaneously through both the inner and outer passages via fittings 491 and 402, respectively. Similarly, deflation time is decreased by applying a negative pressure to both of the fittings 491 and 402, respectively.

A significant advantage of the arrangement of FIG. 10 is the fact that there are provided in a simple, easily manufactured therapeutic catheter structure, a pair of nested parallel and mutually isolated, and mutually sealed, fluid flow passages that may be used for positive purging of air from the interior of the expansible dilation balloon. Either of the inner or outer passages 410, 412 may be used to flow fluid distally into the catheter toward the balloon, while the other is used simultaneously to extract fluid flowing out of the catheter from the balloon. For example, axial fitting 402 may have a pressurized purging fluid applied thereto to flow axially through the hypotube to the dilation balloon. Air or other fluid within the balloon will then flow axially outwardly toward the proximal end of the therapeutic catheter through the outer annular flow passage 412 to flow outwardly through angulated fitting 490. Thus, the arrangement of FIG. 10 makes available a number of alternative procedures in a structure that is easily manufactured and has a compact external configuration. For example, the inner path may be used to flow purging fluid into the catheter while purged fluid is flowed out through the angulated fitting 491. Alternatively, inflation fluid may be caused to flow in through one or both of the inner and outer passages to enhance inflation and deflation time. In still a third mode, a stiffener wire or stylet (not shown in FIG. 10) may be inserted into the hypotube to increase therapeutic catheter stiffness during insertion of the catheter.

In all of the embodiments described herein additional radiopaque marking bands may be applied to the hypotube itself so as to better enable location of the hypotube relative to the therapeutic catheter body tube.

As a typical but non-limiting example of a device constructed according to FIGS. 2 through 8, proximal body tube 42, formed of a 90/10 polyethylene, may have a wall thickness of 0.005 inches, an external diameter of 0.040 inches, and a length of 41.0 inches. Distal body tube 40, formed of a softer 70/30 polyethylene tubing, may have a wall thickness of 0.004 inches, an external diameter of 0.040 inches, and a length of 4.0 inches. The expansible inflation balloon has a length of 1 cm, with the guide tube 62 therein having a wall thickness of 0.004 inches, an outer diameter of 0.024 inches and a total length from its distal opening 64 to its proximal end at the guide wire opening 60 of 4.5 inches.

In a typical example the hypotube of FIGS. 2 through 8 may have an outer diameter of 0.023 inches, a wall thickness of 0.002 inches and a total length to its distal end (not including the solid tapered stiffening wire 84 thereof) of 45.0 inches. The solid tapered stiffening wire 84 may have a total length of 8.0 inches (not including the hypotube).

There have been shown several arrangements of an improved balloon dilation catheter in which a hypotube is positioned within the proximal body tube section, and within part of the distal body tube section, and is arranged to provide a number of advantages, including enhanced pushability, enhanced trackability, faster inflation and deflation time, and, in one arrangement, a positive purging.

I claim:

1. A dilation catheter comprising:
    a body tube having distal and proximal ends and having a guide wire port adjacent said distal end;
    a relatively stiff, metallic hypotube in said body tube having a proximal end and having an open distal end adjacent said guide wire port, said body tube and hypotube collectively forming inner and outer nested fluid flow passages;
    a dilation balloon fixed to said distal end at a position distally of said guide wire port and in fluid communication with the inner and outer nested fluid flow passages to facilitate inflation of said dilation balloon; and
    a connection fixture at the proximal ends of said body tube and hypotube for flowing fluid through said inner and outer flow passages simultaneously.

2. The dilation catheter of claim 1 including a stiffening wire section fixed to the distal end of said hypotube and extending axially therefrom across said guide wire port to provide enhanced stiffening of said catheter in the area of said guide wire port.

3. The dilation catheter of claim 2 including a guide tube in said dilation balloon having an open distal end and having an open proximal end fixed to said guide wire port, and a guide wire extending through said guide tube through said port and along the exterior of said body tube, said stiffening wire section extending across said open proximal end of said guide tube.

4. The dilation catheter of claim 1 wherein said body tube comprises relatively flexible proximal and distal body tube sections fixed to each other in end to end relation at a joint section, said hypotube being formed of a relatively stiff material and having said open distal end thereof positioned adjacent said joint section, said guide wire port being located adjacent said joint section, and a tapered stiffening wire section fixed to the open distal end of said hypotube and extending therefrom axially of said body tube along said joint section and guide wire port.

5. The dilation catheter of claim 4 wherein the proximal end of said hypotube is fixedly secured relative to said catheter body tube.

6. The dilation catheter of claim 1 including an insertable and retractable stylet extending through said hypotube from the proximal end thereof toward its distal end.

* * * * *